(12) United States Patent
Miettinen et al.

(10) Patent No.: US 12,076,589 B2
(45) Date of Patent: *Sep. 3, 2024

(54) METHOD AND APPARATUS FOR USING A MULTI-LAYER MULTI-LEAF COLLIMATOR AS A VIRTUAL FLATTENING FILTER

(71) Applicant: Varian Medical Systems, Inc., Palo Alto, CA (US)

(72) Inventors: Mika Miettinen, San Francisco, CA (US); Ross B. Hannibal, Saratoga, CA (US); Mu Young Lee, San Jose, CA (US)

(73) Assignee: Varian Medical Systems, Inc., Palo Alto, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 18/133,732

(22) Filed: Apr. 12, 2023

(65) Prior Publication Data

US 2023/0241415 A1    Aug. 3, 2023

Related U.S. Application Data

(63) Continuation of application No. 16/369,299, filed on Mar. 29, 2019, now Pat. No. 11,679,278.

(Continued)

(51) Int. Cl.
*A61N 5/10* (2006.01)
*A61B 6/03* (2006.01)
(Continued)

(52) U.S. Cl.
CPC ............ *A61N 5/1065* (2013.01); *A61B 6/032* (2013.01); *A61B 6/06* (2013.01); *A61B 6/4085* (2013.01);
(Continued)

(58) Field of Classification Search
CPC .. A61N 5/1065; A61N 5/1031; A61N 5/1039; A61N 5/1045; A61N 5/1048;
(Continued)

(56) References Cited

U.S. PATENT DOCUMENTS 11,679,278 B2 * 6/2023 Miettinen ................ A61B 6/06
600/427
2004/0034269 A1    2/2004 Ozaki
(Continued)

FOREIGN PATENT DOCUMENTS

| CN | 106540380 A | 3/2017 |
| CN | 107708808 U | 2/2018 |
| JP | 2018000379 A | 1/2018 |

OTHER PUBLICATIONS

Pönisch, Falk et al. "Properties of Unflattened Photon Beams Shaped by a Multileaf Collimator," Medlica Physics, AIP, Melville, NY, US; vol. 33, No. 6; May 18, 2006; pp. 1738-2405.
(Continued)

*Primary Examiner* — Courtney D Thomas
(74) *Attorney, Agent, or Firm* — Fitch, Even, Tabin & Flannery LLP

(57) ABSTRACT

A photon source emits a flattening filter-free photon beam. A control circuit operably couples to a multi-layer multi-leaf collimator that is disposed between the photon source and a treatment area of a patient. The control circuit automatically arranges operation of some, but not all, of the layers of the multi-layer multi-leaf collimator to serve as a virtual flattening filter with respect to the flattening filter-free photon beam emitted by the photon source. By one approach, another of the layers of the multi-layer multi-leaf collimator serves to form a treatment aperture corresponding to a shape of the treatment area of the patient. By one approach the control circuit comprises an integral part of a treatment platform (as versus a dedicated treatment planning platform)

(Continued)

and can carry out most or even essentially all of the planning steps that lead to administration of the treatment to a patient.

19 Claims, 3 Drawing Sheets

Related U.S. Application Data

(60) Provisional application No. 62/650,603, filed on Mar. 30, 2018.

(51) Int. Cl.
*A61B 6/06* (2006.01)
*A61B 6/40* (2024.01)
*G21K 1/04* (2006.01)

(52) U.S. Cl.
CPC .......... *A61N 5/1031* (2013.01); *A61N 5/1039* (2013.01); *A61N 5/1045* (2013.01); *A61N 5/1048* (2013.01); *A61N 5/1078* (2013.01); *G21K 1/046* (2013.01); *A61N 2005/1074* (2013.01); *A61N 2005/1091* (2013.01); *A61N 2005/1095* (2013.01)

(58) Field of Classification Search
CPC .......... A61N 5/1078; A61N 2005/1074; A61N 2005/1091; A61N 2005/1095; A61N 5/1071; A61N 2005/1061; A61N 2005/1085; A61B 6/032; A61B 6/06; A61B 6/4085; G21K 1/046; G21K 1/10
See application file for complete search history.

(56) References Cited

U.S. PATENT DOCUMENTS

| | | |
|---|---|---|
| 2004/0120452 A1 | 6/2004 | Shapiro |
| 2005/0008123 A1 | 1/2005 | Topolnjak |
| 2006/0274885 A1 | 12/2006 | Wang |
| 2007/0086569 A1 | 4/2007 | Johnsen |
| 2012/0043482 A1 | 2/2012 | Prince |
| 2012/0230464 A1 | 9/2012 | Ling |
| 2012/0256103 A1 | 10/2012 | Luzzara |
| 2016/0236010 A1 | 8/2016 | Parsai |
| 2017/0200276 A1 | 7/2017 | Scheib |

OTHER PUBLICATIONS

Extended European Search Report from related European Patent Application No. 19166104.0 dated Jul. 12, 2019; 10 pages.
Chinese Office Action from related Chinese Patent Application No. 201910248675.0 dated Jun. 6, 2022; English translation included; 17 pages.

* cited by examiner

FIG. 2

201 → PROVIDE A PHOTON SOURCE CONFIGURED TO EMIT A FLATTENING FILTER-FREE PHOTON BEAM

202 → PROVIDE A MULTI-LAYER MULTI-LEAF COLLIMATOR DISPOSED BETWEEN THE PHOTON SOURCE AND THE TREATMENT AREA OF THE PATIENT

203 → USE A CONTROL CIRCUIT OPERABLE COUPLED TO THE MULTI-LAYER MULTI LEAF COLLIMATOR TO AUTOMATICALLY ARRANGE OPERATION OF SOME, BUT NOT ALL, OF THE LAYERS OF THE MULTI-LAYER MULTI-LEAF COLLIMATOR TO SERVE AS A VIRTUAL FLATTENING FILTER WITH RESPECT TO THE FLATTENING FILTER-FREE PHOTON BEAM

200

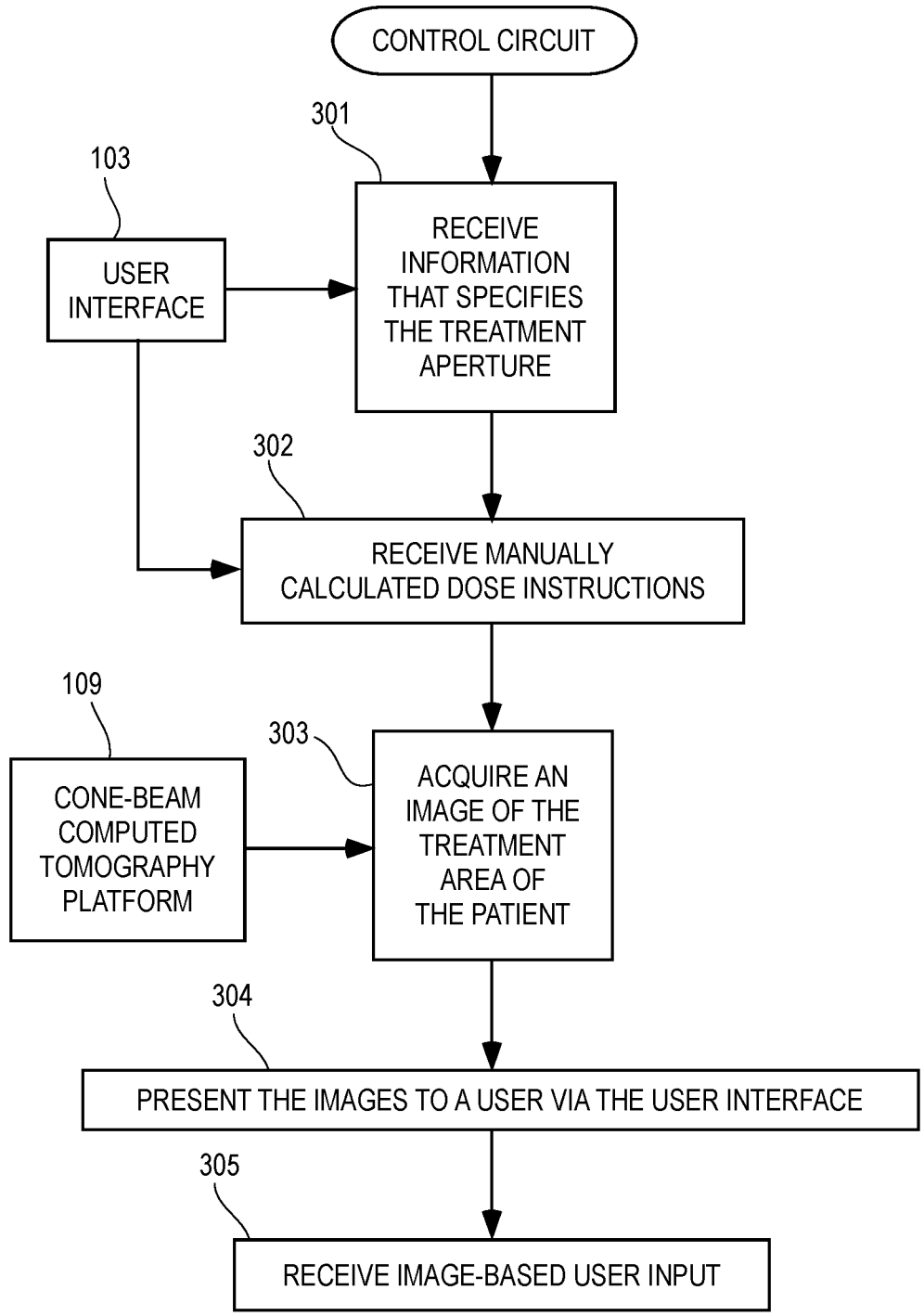

METHOD AND APPARATUS FOR USING A MULTI-LAYER MULTI-LEAF COLLIMATOR AS A VIRTUAL FLATTENING FILTER

CROSS-REFERENCE TO RELATED APPLICATION

This application is a continuation of U.S. patent application Ser. No. 16/369,299, filed Mar. 29, 2019, now U.S. Pat. No. 11,679,278, which claims benefit of U.S. Provisional Application No. 62/650,603, filed Mar. 30, 2018, which are hereby incorporated herein by reference in their entirety.

TECHNICAL FIELD

These teachings relate generally to the use of high-energy photon beams such as x-rays in a patient-treatment application setting.

BACKGROUND

The use of radiation to treat medical conditions comprises a known area of prior art endeavor. For example, radiation therapy comprises an important component of many treatment plans for reducing or eliminating unwanted tumors. Unfortunately, applied radiation does not inherently discriminate between unwanted materials and adjacent tissues, organs, or the like that are desired or even critical to continued survival of the patient. As a result, radiation is ordinarily applied in a carefully administered manner to at least attempt to restrict the radiation to a given target volume.

Treatment plans typically serve to specify any number of operating parameters as pertain to the administration of such treatment with respect to a given patient while using a particular radiation treatment platform. In a typical modern application setting, treatment plans are calculated using iterative optimization approaches.

Although many radiation sources in the past included an integral flattening filter, some prior art practitioners claim that modern optimization algorithms can create any desired dose distribution with or without such a flattening filter. As a result, many modern radiation sources lack an integral flattening filter and hence emit a flattening filter-free beam.

Although suitable for at least some application settings, the foregoing paradigm can nevertheless present challenges. An unflattened beam, for example, can lead to dose fall-off in larger fields. In addition, the necessary calculations are more complex for unflattened beams than flattened beams. This increased complexity can be especially troublesome when time is critical (and even more so when the dosage calculation is manually performed).

BRIEF DESCRIPTION OF THE DRAWINGS

The above concerns are at least partially met through provision of the method and apparatus for using a multi-layer multi-leaf collimator as a virtual flattening filter described in the following detailed description, particularly when studied in conjunction with the drawings, wherein:

FIG. 2 comprises a flow diagram as configured in accordance with various embodiments of these teachings; and FIG. 3 comprises a flow diagram as configured in accordance with various embodiments of these teachings.

Figure 1:
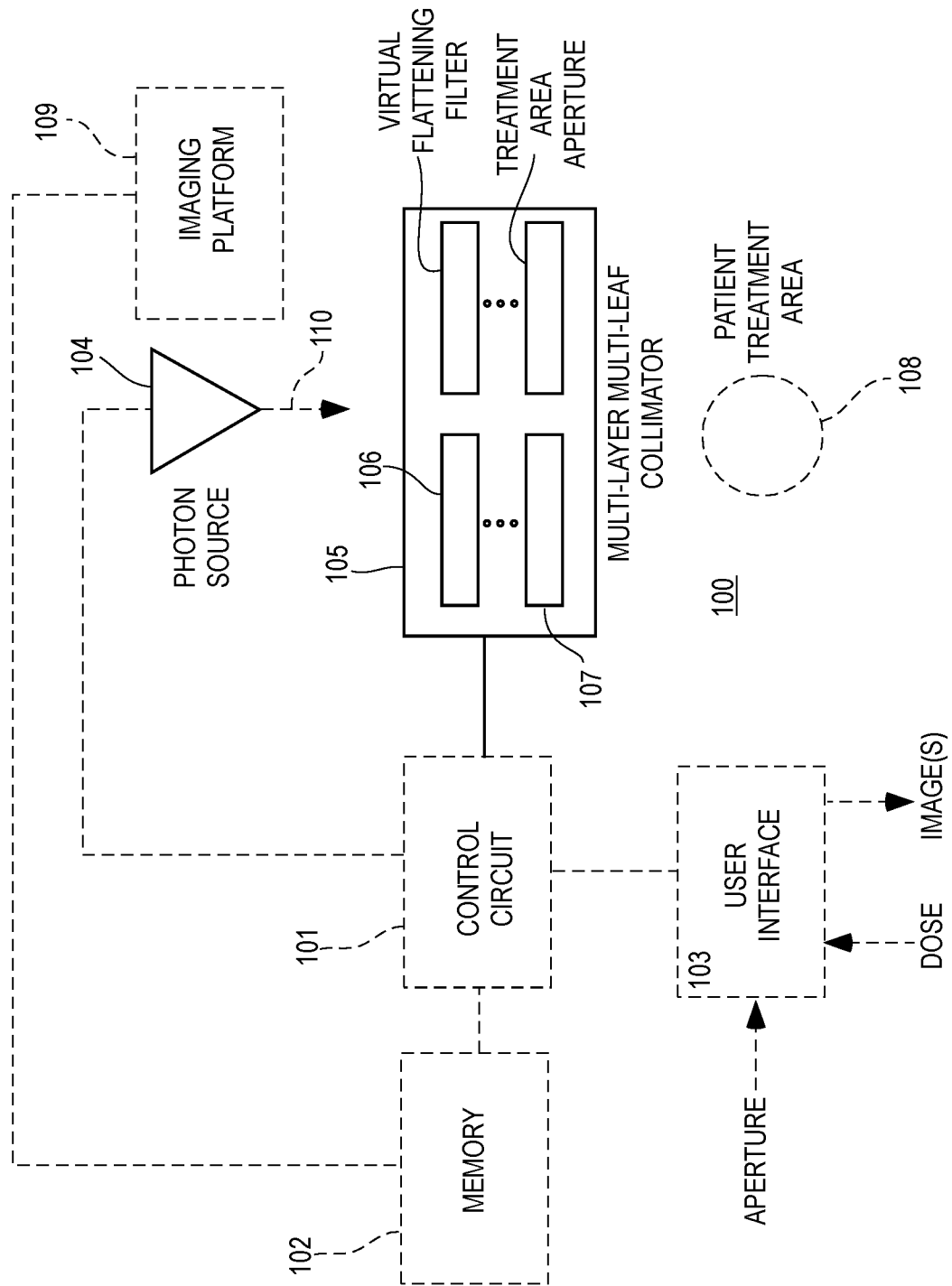
FIG. 1 comprises a block diagram as configured in accordance with various embodiments of these teachings.

Elements in the figures are illustrated for simplicity and clarity and have not necessarily been drawn to scale. For example, the dimensions and/or relative positioning of some of the elements in the figures may be exaggerated relative to other elements to help to improve understanding of various embodiments of the present teachings. Also, common but well-understood elements that are useful or necessary in a commercially feasible embodiment are often not depicted in order to facilitate a less obstructed view of these various embodiments of the present teachings. Certain actions and/or steps may be described or depicted in a particular order of occurrence while those skilled in the art will understand that such specificity with respect to sequence is not actually required. The terms and expressions used herein have the ordinary technical meaning as is accorded to such terms and expressions by persons skilled in the technical field as set forth above except where different specific meanings have otherwise been set forth herein.

DETAILED DESCRIPTION

Generally speaking, these various embodiments presume use of a photon source configured to emit a flattening filter-free photon beam. A control circuit operably couples to a multi-layer multi-leaf collimator that is disposed between the photon source and a treatment area of a patient. The control circuit automatically arranges operation of some, but not all, of the layers of the multi-layer multi-leaf collimator to serve as a virtual flattening filter with respect to the flattening filter-free photon beam emitted by the photon source. By one approach, another of the layers of the multi-layer multi-leaf collimator serves to form a treatment aperture corresponding to a shape of the treatment area of the patient.

By one approach, the multi-layer multi-leaf collimator comprises a two-layer multi-leaf collimator. In such a case, one of the multi-leaf layers serves as a virtual flattening filter while the other of the multi-leaf layers is employed as a treatment volume shape-matching aperture.

These teachings are highly flexible in practice and will accommodate various modifications and embellishments. By one approach, the control circuit can receive manually calculated dose instructions to be used when applying radiation to the patient's treatment area. In lieu of the foregoing or in combination therewith, the control circuit can receive, from a user, information that defines the treatment aperture for a layer of the multi-layer multi-leaf collimator that is not serving as a virtual flattening filter. By yet another approach, and again in lieu of the foregoing or in combination therewith, the control circuit can be configured to present an image corresponding to the patient's treatment area to a user via a user interface.

These and other benefits may become clearer upon making a thorough review and study of the following detailed description. Referring now to the drawings, and in particular to FIG. 1, an illustrative apparatus 100 that is compatible with many of these teachings will now be presented.

In this illustrative example the enabling apparatus 100 includes a control circuit 101. Being a "circuit," the control circuit 101 therefore comprises structure that includes at least one (and typically many) electrically-conductive paths (such as paths comprised of a conductive metal such as copper or silver) that convey electricity in an ordered manner, which path(s) will also typically include corresponding electrical components (both passive (such as resistors and capacitors) and active (such as any of a variety of semiconductor-based devices) as appropriate) to permit the circuit to effect the control aspect of these teachings.

Such a control circuit 101 can comprise a fixed-purpose hard-wired hardware platform (including but not limited to an application-specific integrated circuit (ASIC) (which is an integrated circuit that is customized by design for a particular use, rather than intended for general-purpose use), a field-programmable gate array (FPGA), and the like) or can comprise a partially or wholly-programmable hardware platform (including but not limited to microcontrollers, microprocessors, and the like). These architectural options for such structures are well known and understood in the art and require no further description here. This control circuit 101 is configured (for example, by using corresponding programming as will be well understood by those skilled in the art) to carry out one or more of the steps, actions, and/or functions described herein.

By one approach the apparatus 100 and this control circuit 101 are all part of a radiation treatment machine. In this case the control circuit 101 is not a physically and logically discrete component that is dedicated to treatment planning rather than treatment administration.

By one approach the control circuit 101 operably couples to an optional memory 102. This memory 102 may be integral to the control circuit 101 or can be physically discrete (in whole or in part) from the control circuit 101 as desired. This memory 102 can also be local with respect to the control circuit 101 (where, for example, both share a common circuit board, chassis, power supply, and/or housing) or can be partially or wholly remote with respect to the control circuit 101 (where, for example, the memory 102 is physically located in another facility, metropolitan area, or even country as compared to the control circuit 101).

In addition to image data as described herein, this memory 102 can serve, for example, to non-transitorily store the computer instructions that, when executed by the control circuit 101, cause the control circuit 101 to behave as described herein. (As used herein, this reference to "non-transitorily" will be understood to refer to a non-ephemeral state for the stored contents (and hence excludes when the stored contents merely constitute signals or waves) rather than volatility of the storage media itself and hence includes both non-volatile memory (such as read-only memory (ROM) as well as volatile memory (such as an erasable programmable read-only memory (EPROM).)

By another optional approach (in lieu of the foregoing or in combination therewith) the control circuit 101 operably couples to a user interface 103. This user interface 103 can comprise any of a variety of user-input mechanisms (such as, but not limited to, keyboards and keypads, cursor-control devices, touch-sensitive displays, speech-recognition interfaces, gesture-recognition interfaces, and so forth) and/or user-output mechanisms (such as, but not limited to, visual displays, audio transducers, printers, and so forth) to facilitate receiving information and/or instructions from a user and/or providing information to a user.

The enabling apparatus 100 also includes a photon source 104. This photon source 104 can comprise, for example, an x-ray source such as a radio-frequency (RF) linear particle accelerator-based (linac-based) x-ray source (such as the Varian Linatron M9). A linac is a type of particle accelerator that greatly increases the kinetic energy of charged subatomic particles or ions by subjecting the charged particles to a series of oscillating electric potentials along a linear beamline, which can be used to generate ionizing radiation (e.g., X-rays) and high energy electrons.

In this example the photon source 104 comprises a flattening filter-free photon source and hence the emitted beam 110 constitutes a flattening filter-free beam. Unlike a source that produces a flattened beam, the flattening filter-free beam is more rounded or pointed by way of comparison. Flattening filter-free beams typify a modern radiation treatment system for a variety of reasons.

The photon source 104 may, or may not as desired, operably couple to the control circuit 101. The control circuit 101 may be operably coupled to the photon source 104 in order to facilitate automated control of the photon source 104 by the control circuit 101.

These teachings presume the use of at least one multi-layer multi-leaf collimator 105 that is operably coupled to and controlled, at least in part, by the control circuit 101. Multi-leaf collimators are comprised of a plurality of individual parts (known as "leaves") that are formed of a high atomic numbered material (such as tungsten) that can move independently in and out of the path of the radiation-therapy beam in order to selectively block (and hence shape) the beam. Typically the leaves of a multi-leaf collimator are organized in pairs that are aligned collinearly with respect to one another and which can selectively move towards and away from one another. A typical multi-leaf collimator has many such pairs of leaves, often upwards of twenty, fifty, or even one hundred such pairs.

In the present case, being a multi-layer multi-leaf collimator, the collimator comprises two or more multi-leaf collimators having a stacked relationship with respect to one another. In this illustrative example, the proximal multi-leaf collimator (i.e., the multi-leaf collimator that is closest to the photon source 104) is denoted by reference numeral 106 and the distal multi-leaf collimator (i.e., the multi-leaf collimator that is furthest from the photon source 104) is denoted by reference numeral 107. The multi-layer multi-leaf collimator 105 may include additional multi-leaf collimators between the proximal multi-leaf collimator 106 and the distal multi-leaf collimator 107 as desired. (Multi-leaf collimators, including multi-layer multi-leaf collimators, are known in the art. Accordingly, for the sake of brevity no further elaboration in these regards is provided here.)

So configured, a patient treatment area 108 (i.e., a target volume in or on a patient such as a tumor) can be exposed to the beam 110 after the latter has passed through the multi-layer multi-leaf collimator 105.

The application setting may include other components such as an imaging platform 109 that is configured to acquire an image of, for example, the patient treatment area 108. The imaging platform 109 may comprise, for example, a cone-beam computed tomography imaging platform. So configured the imaging platform 109 can provide corresponding images (such as cone-beam computed tomography images) to the memory 102 and/or the control circuit 101. These images can be employed as described herein.

The application setting may also include other components that are not illustrated. Examples include but are not limited to one or more support surfaces (such as a couch) to support the patient during the treatment session and a gantry or other mechanism to permit selective movement of the photon source 104. As the foregoing elements and systems are well understood in the art, further elaboration in these regards is not provided here except where otherwise relevant to the description.

With continued reference to FIG. 1, FIG. 2 presents a process 200 that can be carried out using the above-described apparatus 100.

At block 201, this process 200 provides a photon source as described above configured to emit a flattening filter-free photon beam. And at block 202, this process 200 provides a multi-layer multi-leaf collimator disposed between the photon source and the treatment area of the patient, again as described above. At block 203, this process 200 then uses the aforementioned control circuit 101 to automatically arrange operation of some, but not all, of the layers of the multi-layer multi-leaf collimator 105 to serve as a virtual flattening filter with respect to the flattening filter-free photon beam 110.

The virtual flattening filter serves to flatten the beam 110. By one approach the control circuit 101 automatically arranges operation of this multi-layer multi-leaf collimator 106 to serve as a virtual flattening filter by automatically calculating at least one dynamic multi-leaf collimator motion pattern.

In this illustrative example, the control circuit 101 uses only one of the multi-leaf collimators 106 as a virtual flattening filter. If desired, and when the multi-layer multi-leaf collimator 105 includes more than two multi-leaf collimators, the control circuit 101 can use more than one of the multi-leaf collimators for the virtual flattening filter so long as at least one of the multi-leaf collimators is not used in this manner.

In this illustrative example, the control circuit 101 uses the remaining multi-leaf collimator 107 to form a treatment area aperture. This use of a multi-leaf collimator is well understood in the art and consists of arranging the elements of the multi-leaf collimator to define a treatment aperture that corresponds to a relevant shape of the patient treatment area 108. So configured, the radiation beam 110 is conformally shaped to better match the shape of the patient treatment area 108 to thereby avoid or at least mitigate irradiating adjacent tissues on the lateral sides (in the beam's eye view) of the patient treatment area 108.

Use of the multi-layer multi-leaf collimator 105 as described above can be further supplemented and/or informed by other information. FIG. 3 provides some illustrative examples in these regards.

At block 301, the control circuit 101 receives, via the aforementioned user interface 103, information that defines the aforementioned treatment aperture for the layer of the multi-layer multi-leaf collimator 105 that is not serving as the virtual flattening filter. This information may be directly sourced by a user or may be partially or wholly automatically calculated by the control circuit 101 using other relevant information.

At block 302, the control circuit 101 receives, again via the aforementioned user interface 103, manually calculated dose instructions to be used when applying radiation to the treatment area 108 of the patient. These manually calculated dose instructions may comprise, for example, manually calculated monitor unit (MU)-based instructions. Manually calculated dose instructions would typically be a difficult or even impossible expectation. The use of the virtual flattening filter to flatten the beam, however, greatly simplifies the necessary calculations in these regards and makes manual calculations both reasonable and practical from the standpoint of time requirements. (This reference to manual calculations will be understood to not preclude calculations made by a person using such tools as a hand-held/hand-manipulated calculator.)

At block 303, an image of the treatment area of the patient can be acquired via, for example, the aforementioned imaging platform 109. As mentioned above, this imaging platform 109 can comprise, if desired, a cone-beam computed tomography platform. In such a case one or more digital, orthogonal radiographs can be reconstructed from the cone-beam computed tomography information to yield the desired image. At block 304, the control circuit 101 presents the acquired image to a user via the user interface 103. At block 305 the control circuit 101 then receives image-based user input as entered via the user interface 103. As an illustrative example, the user may employ a touch-screen to encircle the patient treatment area 108 in such an image. The control circuit 101 may then use that information when forming the above-described treatment aperture.

These teachings can offer a relatively extreme reduction of time in the setup and planning stages of a radiation treatment plan. At least a significant part of these time savings are owing to the creation and use of a virtual flattening filter to thereby simplify the calculations that would otherwise be necessary when using a flattening filter-free beam. Other time savings can be expected from the above-described automated activity.

A relatively simple example may help illustrate these advantages. In many use cases radiation is applied to cure a particular patient's condition (by, for example, destroying a malignant tumor). There are other use cases, however, where a cure is neither intended nor reasonably expected. For example, radiation may be applied in a palliative context to relieve a patient's extreme pain. In such an application context, where the patient's life expectancy is often no better than very short-term, radiation can quell the patient's sensations of pain and collateral tissue damage owing to the radiation can be accepted as not greatly worsening the patient's overall quality of life or life expectancy.

Upon a patient presenting themselves as just described above, the above-described apparatus 100 can operate in nearly a completely automated manner to provide a palliative radiation treatment. Upon a user activating this capability, the control circuit 101 could employ the imaging platform 109 to acquire a relevant patient outline and develop the appropriate radiation prescription and plan to generate a patient-specific uniform dose at midline (based, for example, upon ray tracing-based electronic compensation). The control circuit 101 could then employ that solution when treating the patient with the resultant beam 110.

By utilizing the virtual flattening filter, the overall calculation time can be significantly reduced to only a small fraction of what might otherwise be required. While time savings are often viewed positively, minutes (or hours) saved can be especially important to a patient who is suffering with extreme pain.

The following description provides a more specific and detailed example. It will be understood that no particular limitations are intended by way of the specific details of this example.

The control circuit 101 can acquire a cone-beam computed tomography image using the imaging platform 109. Digital, orthogonal radiographs can be reconstructed from that data and displayed via the user interface 103 to the clinician. The clinician can select the center of the treatment area (i.e., the treatment isocenter) using the orthogonal view and a digital graticule and then apply any necessary shifts to move the patient to a defined treatment position (for example, by moving a couch upon which the patient rests). The clinician can then add a treatment field and defines the gantry and collimator angle for that field.

The control circuit 101 can then facilitate an automatic digitally reconstructed radiograph using a beam's eye view to present a corresponding image with isocenter information to the clinician via the user interface 103. The clinician can then define the treatment aperture using that image. The control circuit 101 can then utilize a corresponding multi-leaf collimator 107 to form that aperture. The control circuit 101 can then also automatically arrange operation of another multi-leaf collimator 106 to serve as a virtual flattening filter.

The control circuit 101 can then provide an estimated equivalent square field size for an irregular multi-leaf collimator beam aperture and the clinician can be provided with an option to create an opposed/mirrored field. The clinician can measure the depth of the isocenter point for each field (i.e., the skin to isocenter distance from the beam direction) and use the known source to axis distance, measured depth, equivalent square field size, virtual flattening filter monitor unit-factor, and relevant tabulated data to manually calculate the required monitor units to reach the prescribed dose into the isocenter. That (or those) monitor unit value(s) can then be entered by the clinician via the user interface 103 for each field and the patient then accordingly treated.

Those skilled in the art will recognize that a wide variety of modifications, alterations, and combinations can be made with respect to the above described embodiments without departing from the scope of the invention, and that such modifications, alterations, and combinations are to be viewed as being within the ambit of the inventive concept.

What is claimed is:

1. An apparatus for sourcing a photon beam towards a treatment area of a patient, the apparatus comprising:
    a photon source configured to emit a photon beam;
    a multi-layer multi-leaf collimator disposed between the photon source and the treatment area of the patient;
    a control circuit operably coupled to the multi-layer multi-leaf collimator and configured to automatically arrange operation of some, but not all, of the layers of the multi-layer multi-leaf collimator to serve as a virtual flattening filter with respect to the photon beam.

2. The apparatus of claim 1 wherein the control circuit is configured to automatically arrange operation of some, but not all, of the layers of the multi-layer multi-leaf collimator to serve as a virtual flattening filter by automatically calculating at least one dynamic multi-leaf collimator motion pattern.

3. The apparatus of claim 1 further comprising:
    a user interface operably coupled to the control circuit;
    and wherein the control circuit is further configured to receive, via the user interface, information that defines a treatment aperture for a layer of the multi-layer multi-leaf collimator that is not serving as the virtual flattening filter.

4. The apparatus of claim 3 wherein the treatment aperture corresponds to a shape of the treatment area of the patient.

5. The apparatus of claim 3 wherein the control circuit is further configured to receive, via the user interface, manually calculated dose instructions to be used when applying radiation to the treatment area of the patient.

6. The apparatus of claim 5 wherein the manually calculated dose instructions comprise manually calculated monitor unit (MU)-based instructions.

7. The apparatus of claim 3 wherein the apparatus is further configured to acquire an image of the treatment area of the patient and the control circuit is further configured to present the image via the user interface to thereby facilitate using the photon beam to treat the treatment area.

8. The apparatus of claim 7 wherein the image comprises a cone-beam computed tomography image.

9. The apparatus of claim 1 wherein the multi-layer multi-leaf collimator comprises a two-layer multi-leaf collimator.

10. A method for sourcing a photon beam towards a treatment area of a patient, the method comprising:
    providing a photon source configured to emit a photon beam;
    providing a multi-layer multi-leaf collimator disposed between the photon source and the treatment area of the patient;
    using a control circuit operably coupled to the multi-layer multi-leaf collimator to automatically arrange operation of some, but not all, of the layers of the multi-layer multi-leaf collimator to serve as a virtual flattening filter with respect to the photon beam.

11. The method of claim 10 wherein automatically arranging operation of some, but not all, of the layers of the multi-layer multi-leaf collimator to serve as a virtual flattening filter comprises automatically calculating at least one dynamic multi-leaf collimator motion pattern.

12. The method of claim 10 wherein providing the multi-layer multi-leaf collimator comprises providing a two-layer multi-leaf collimator.

13. The method of claim 12 wherein automatically arranging operation of some, but not all, of the layers of the multi-layer multi-leaf collimator to serve as the virtual flattening filter comprises arranging operation of only one of the two layers of the two-layer multi-leaf collimator to serve as the virtual flattening filter.

14. The method of claim 13 further comprising:
    defining a treatment aperture that corresponds to a shape of the treatment area of the patient using a layer of the two-layer multi-leaf collimator that is not serving as the virtual flattening filter.

15. The method of claim 14 further comprising:
    providing a user interface operably coupled to the control circuit;
    receiving at the control circuit, via the user interface, information that specifies the treatment aperture.

16. The method of claim 15 further comprising:
    receiving at the control circuit, via the user interface, manually calculated dose instructions to be used when applying radiation to the treatment area of the patient.

17. The method of claim 16 wherein the manually calculated dose instructions comprise manually calculated monitor unit (MU)-based instructions.

18. The method of claim 15 further comprising:
    acquiring an image of the treatment area of the patient and presenting the image to a user via the user interface to thereby facilitate using the photon beam to treat the treatment area.

19. The method of claim 18 wherein acquiring the image comprises acquiring a cone-beam computed tomography image.

* * * * *